(12) United States Patent
Doubochinski et al.

(10) Patent No.: US 7,531,131 B2
(45) Date of Patent: May 12, 2009

(54) METHOD AND VIBRATING DEVICE FOR CONDITIONING, AIR-CONDITIONING, COOLING AND DECONTAMINATING, DISINFECTING AND STERILIZATION PHYSICAL MEDIA

(75) Inventors: Danil Doubochinski, 86 rue de Wattignies, 75012 Paris (FR); Roman Prytkov, Minsk (BY)

(73) Assignees: Tamara Touzova, Paris (FR); Danil Doubochinski, Paris (FR)

( * ) Notice: Subject to any disclaimer, the term of this patent is extended or adjusted under 35 U.S.C. 154(b) by 1060 days.

(21) Appl. No.: 10/149,696

(22) PCT Filed: Dec. 7, 2000

(86) PCT No.: PCT/FR00/03439

§ 371 (c)(1),
(2), (4) Date: Mar. 25, 2003

(87) PCT Pub. No.: WO01/41817

PCT Pub. Date: Jun. 14, 2001

(65) Prior Publication Data

US 2003/0161754 A1 Aug. 28, 2003

(30) Foreign Application Priority Data

Dec. 10, 1999 (FR) .................. 99 15584

(51) Int. Cl.
| | |
|---|---|
| *A61L 9/00* | (2006.01) |
| *A61L 2/08* | (2006.01) |
| *A61L 2/00* | (2006.01) |
| *A62B 7/08* | (2006.01) |
| *B01J 19/08* | (2006.01) |
| *B05B 1/08* | (2006.01) |
| *B01D 47/06* | (2006.01) |
| *F26B 3/08* | (2006.01) |
| *F24F 3/16* | (2006.01) |
| *F25D 17/06* | (2006.01) |
| *F25B 15/00* | (2006.01) |
| *F25B 41/00* | (2006.01) |
| *F25J 3/00* | (2006.01) |

(52) U.S. Cl. ............... 422/1; 422/4; 422/5; 422/26; 422/28; 422/121; 422/123; 422/125; 422/186.04; 422/298; 422/300; 422/305; 422/306; 239/102.2; 261/78.1; 236/338; 34/372; 62/78; 62/94; 62/95; 62/141; 62/657; 62/513

(58) Field of Classification Search ............ 422/1, 422/4–5, 26, 28, 121, 123, 125, 186.04, 298, 422/300, 305–306; 239/102.2; 236/338; 34/372; 261/78.1; 62/78, 94–95, 141, 657, 62/513

See application file for complete search history.

(56) References Cited

U.S. PATENT DOCUMENTS 2,289,035 A * 7/1942 Neeson .................. 62/183

(Continued)

FOREIGN PATENT DOCUMENTS

GB      EP 0 774 263 A1 * 5/1997

(Continued)

*Primary Examiner*—Jill Warden
*Assistant Examiner*—Monzer R. Chorbaji
(74) *Attorney, Agent, or Firm*—Young & Thompson

(57) ABSTRACT

A method using vibration for conditioning, air-conditioning, cooling and decontaminating, disinfecting and sterilizing physical media. The method includes a first vibratory action (13) performed on a regulated incoming current of the physical medium (2) so that the flow of the physical medium (2) is formed and the necessary and adequate conditions for cooling are created; a refrigerating medium (3) and a cold-absorbing medium (6) interact in a heat exchanging system (1); and another vibratory action (10) is performed on a cold-absorbing medium in order that the physical medium is continuously and/or periodically decontaminated and the necessary and adequate conditions for the functioning of the decontamination system in its steady state are created.

15 Claims, 1 Drawing Sheet

U.S. PATENT DOCUMENTS

| | | | | | |
|---|---|---|---|---|---|
| 2,913,184 | A | * | 11/1959 | Parlin | 236/44 A |
| 4,689,515 | A | * | 8/1987 | Benndorf et al. | 310/316.01 |
| 5,527,459 | A | | 6/1996 | Ikeda et al. | 422/121 |
| 5,653,919 | A | * | 8/1997 | White et al. | 261/21 |
| 5,938,823 | A | * | 8/1999 | Condit et al. | 96/16 |

FOREIGN PATENT DOCUMENTS

| | | | |
|---|---|---|---|
| JP | 54111161 | * | 8/1979 |
| JP | 62282686 | | 12/1987 |
| JP | 63123343 | | 5/1988 |

* cited by examiner

METHOD AND VIBRATING DEVICE FOR CONDITIONING, AIR-CONDITIONING, COOLING AND DECONTAMINATING, DISINFECTING AND STERILIZATION PHYSICAL MEDIA

BACKGROUND OF THE INVENTION

The invention is related to the domain of conditioning, air conditioning, cooling and decontamination, of disinfection, sterilisation of physical media by vibratory actions and concerns a process and devices allowing the performing of such functions.

The invention is applicable to the liquid, gas media and to the mixed media composed by liquids, gases and colloidal and solid substances. Elements treated by the vibratory actions and elements performing calorific exchanges can be represented by cooling agents constituted by liquid, gas, solid and mixed, organic and/or not organic media, whereas the vibratory actions performing the conditioning, the air conditioning, the cooling and the decontamination, the disinfection, the sterilisation of aforesaid physical media can be represented by mechanical, electromechanical, ultrasound, magnetic, electromagnetic and mixed vibratory systems.

DESCRIPTION OF THE RELATED ART

Processes and devices of conditioning, air conditioning, cooling and decontamination, disinfection, sterilisation of physical media used in conditioners, air-conditioners, refrigerating devices and current systems of decontamination are known (see U.S. Pat. No. 5,527,459).

The essential inconveniences of the existing processes and devices are the following ones: significant energy consumption; weak efficiency and return; complex construction; long cycle duration; high costs of the installations and of their exploitation; pollution and significant noise; significant volume and necessary surface for the achievement of these functions; weak level of protection against contamination—which after all limits their practical applications.

SUMMARY OF THE INVENTION

The invention's process and the device for its implementation, are lacking the aforementioned inconveniences, importantly simplifying the principles and the systems performing them, and consequently increasing the return of devices and decreasing several times the time and energy spent for the tasks of conditioning, air conditioning, cooling and decontamination, disinfection, sterilisation of physical media.

Thus the invention has for one object, a vibratory process of conditioning, air conditioning, cooling and decontamination, disinfection, sterilisation of physical media, characterised by the fact that:

By at least first vibratory action, one acts on the regulated input stream of the physical media represented by refrigerating agents and by at least a second vibratory action on the same physical media in a cold room and therefore, one forms the stream of cooled physical media and one creates the necessary and sufficient conditions of its cooling, One forms an interaction between at least one cooling medium and at least one cold-absorbing medium, According to other characteristics of the invention:

By at least a third vibratory action, one acts on a cold-absorbing medium and therefore, one disinfects in a continuous or/and periodical way this physical medium and one creates the necessary and sufficient conditions of the functioning of the system of decontamination in stationary mode, By at least a fourth action, one acts on a cold-absorbing medium and therefore, one achieves the necessary and sufficient conditions to form at least one closed circuit of the traffic of the cold-absorbing physical medium by regulating with a regulation device, By at least a fifth action, one acts on a cooling medium and therefore, one achieves the necessary and sufficient conditions to form at least one closed circuit of the traffic of the cooled physical medium by regulating with a regulation device, One feeds the vibratory action systems with the energy of at least one source in optimal mode and therefore one achieves the necessary and sufficient conditions of the vibratory treatment of the physical medium to perform the effective modes of regulated functioning of the systems of conditioning, air conditioning, cooling and decontamination, disinfection, physical sterilisation of media.

The invention has also for another object, a process of vibratory treatment—such as defined above—, which acts on at least one cooling physical medium by modifying its state of aggregate and which presents the following characteristics:

By at least one vibratory mechanical, pneumatic, hydraulic, electric, magnetic, electromagnetic, acoustic or mixed action, one acts on the physical medium cool, one micronises and one divides the physical medium in the form of vapor and/or aerosol constituted by particles with dimensions lower than the micron, By at least one vibratory action on the micronised cooled physical medium, this medium is recovered in order to be used in a closed circuit with the help of the device in regulated mode.

According to other characteristics:

One acts in an additional way on the stream of the cold-absorbing physical medium by a vibratory action—notably by a hard radiation or by a magnetic radiation, or still by an electromagnetic and/or mixed radiation—, thus one creates additional conditions favouring its decontamination, its disinfection and its sterilisation.

The invention has besides for as a still further object, a device for the implementation of the process defined above, which contains at least: a first system of vibratory action system and a second vibratory action system fed by an energy source and acting on a regulated stream of the physical medium represented by refrigerating agents in a cold chamber; a closed circuit of the traffic of the cooling physical medium and the system of regulation by a regulation device; a closed circuit of the traffic of the cold-absorbing physical medium and the system of regulation of by a regulation device; a cold chamber and a heat exchanger performing the interaction between at least one cooling medium and at least one cold-absorbing medium; at least a vibratory system of decontamination, disinfection and sterilisation of physical media.

According to other characteristics:

The first and second systems are reunited in a single vibratory action system,

The first and second vibratory action systems are set in motion by the energy of the regulated stream of the physical medium, notably when the first and second systems are achieved in the form of a siren or of a whistle, The cold chamber and the heat exchanger are reunited in a single system of exchange of heat, The regulated gates and/or suction pumps constitute the systems of regulation of the physical media.

The invention has finally for object, a device for the implementation of the process defined above, characterised by the fact that it contains at least: a first vibratory action system, notably of electromagnetic and/or thermic radiation, which acts on the regulated streams of the physical media; a second vibratory action system, notably of mechanical, pneumatic, hydraulic, magnetic, electric, ultrasound or mixed type, performing the micronisation of the physical medium in a treatment chamber, for instance a cold and/or an acoustic chamber, or still a heat exchange chamber (heat exchanger), or a mixed chamber, and pulverising it in the form of vapor or of aerosol by a pulverisation system, which represents at least a cooling and/or freezing system of the cooling medium, at least a closed circuit of the traffic of the cooling physical medium and at least a system of regulation by a device of regulation constituted by a regulated gate and/or by a suction pump; at least a closed circuit of the traffic of the cold-absorbing physical medium and at least a system of regulation by a regulation device constituted by a regulated gate and/or by a suction pump; a cold chamber and at least a heat exchanger performing the interaction between at least a cooling medium and at least a cold-absorbing medium; at least a vibratory system of decontamination, disinfection and sterilisation of physical media.

BRIEF DESCRIPTION OF THE DRAWING

On FIG. 1 are represented in broad outline the schematic view of the devices operating the invention's process of conditioning, air conditioning, cooling and decontamination, disinfection, sterilisation of physical media.

DESCRIPTION OF THE PREFERRED EMBODIMENTS

Figure 1:
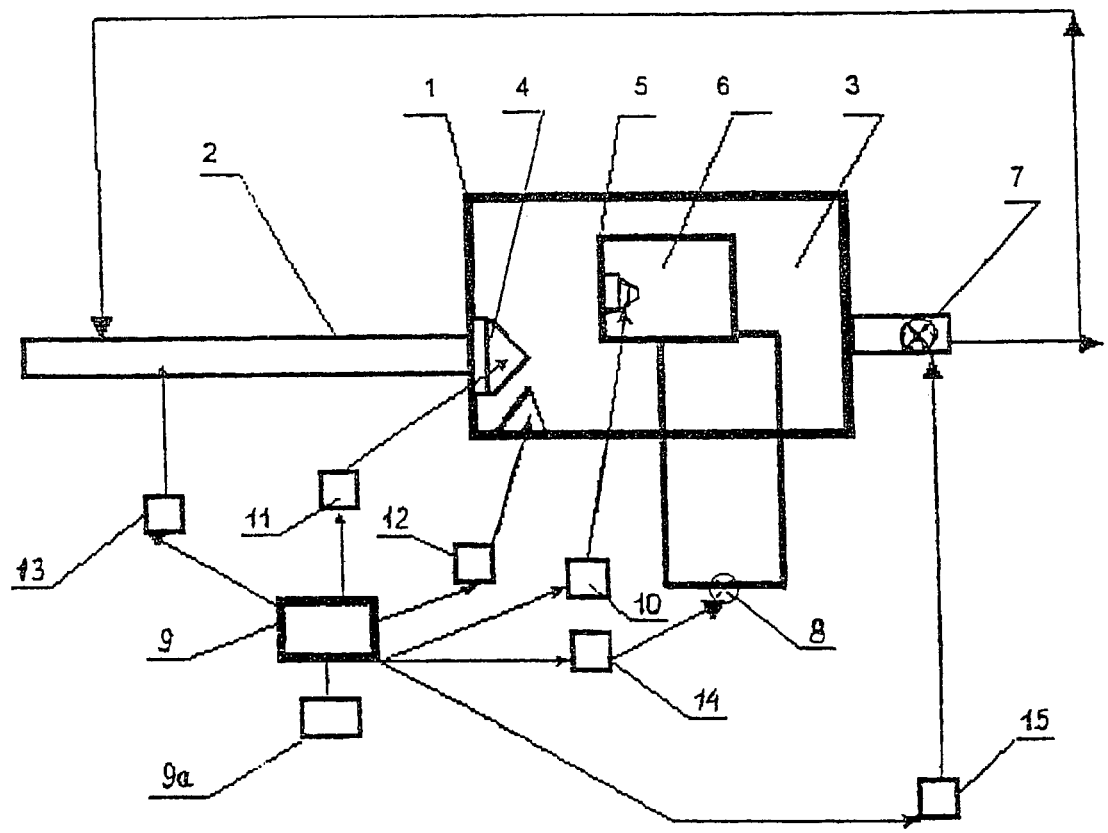

The device represented on FIG. 1 contains:

a heat exchange system (heat exchanger) 1 in which a regulated input stream of a physical medium 2 is cooled and forms a cooling medium 3, a vibration treatment system 4, at least one chamber 5 constituting a volume in which the cold-absorbing medium 6 accumulates, a device 7 performing the regulated evacuation and/or circulation of the cooling medium stream 3, (e.g., a regulated gate and/or evacuation pump), a device 8 performing a regulated stream of the cold-absorbing medium 6, (e.g., a regulated gate and/or evacuation pump), at least one power supply source 9, which can be adjusted by an electronic regulation 9a, of external vibratory action systems 10, 11, 12, and 13 performing the vibratory actions respectively on the input stream of the physical medium 2, on the cooling medium 3, on the cold-absorbing medium 6 and on the vibration treatment system 4 of the physical medium 2, and at least one system 14, 15 performing the regulated evacuation and/or circulation of the cooling medium stream 3 and of the cold-absorbing medium 6 by the systems 7 and 8.

The physical medium 2 can consist of a liquid, gas medium or by a mixture of organic and/or inorganic substances, in the composition of which can include liquids, gases, colloidal or solid bodies or a combination of the aforementioned substances.

The cold-absorbing medium 6 consist of a liquid, gas medium or by a mixture of organic and/or inorganic substances of liquid, gas, colloidal and solid type or combinations of such substances.

The vibratory action systems 11, 12, 13 can be at least one device of ultrasound action, for instance a siren, a whistle, a piezo-electric vibrator or a combination of the aforementioned devices, of at least one device of magnetostriction type, one device of magnetic or electromagnetic type, creating for instance a magnetic or electromagnetic field of corresponding configuration or intensity, or, finally, various combinations of aforementioned devices and systems. Vibratory action systems 10 can be at least one magnetic or electromagnetic device, creating for example a magnetic or electromagnetic field of configuration or intensity corresponding to the need of decontamination, disinfection, sterilisation of physical media. The system 15 provides the regulated evacuation and/or circulation of the cooling medium stream 3 by the system 7. The system 14 provides the regulated evacuation and/or circulation of the regulated stream of cold-absorbing medium 6 by the system 8. The power supply system 9 provides the indispensable modes of functioning of the systems 10,11,12,13,14 and 15 and includes the regulator 9a, which allows varying the frequencies and the energy amplitudes according to the modes of functioning of these systems. In this way the systems 9 and 9a can provide the regulation of the device by variation of the frequency and of the amplitude of the actions on the treated media 2, 3 and on the devices regulating the evacuation and the circulation of these media. The streams of the treated medium 2 can be used as a source of energy to supply the system 4.

The vibratory actions 11, 12, 13 can be performed by a unique vibrator or system.

The vibratory treatment device 4 can contain:

At least a device performing the micronisation and the pulverising with fine dispersal of the physical medium 2, for example a mechanical and/or acoustics, and/or pneumatic, and/or still hydraulic or mixed atomiser 4 which scatters and injects the physical medium 2 in the form of vapor or aerosol with dimensions of particles (droplets) of the molecular level (lower than the micron).

In that case, the expensive and energy-wasting traditional process is replaced by a technology of injection with weak dispersal that is characterised by decreasing the energy and time consumptions to be ten times and even thousand times less.

So, the chamber 1 can be constituted by an acoustic chamber of microniser, the device of vibratory treatment 4 is a system including a syringe which pulverises the physical medium 2 with fine dispersal.

According to the plan represented in the FIG. 1, the vibratory process of conditioning, air conditioning, cooling and decontamination, disinfection, sterilisation of physical medium is implemented in the following way.

The regulated stream of the physical medium 2 enters into the chamber 1 of the heat exchange system.

During its movement, the physical medium is subjected to at least one vibratory action 11 at once before its introduction in the chamber 1, and then in the chamber 5 itself by the system 12. The aforesaid actions 11 and 12 create the conditions of cooling of the medium 2 under the effect of the mechanical, pneumatic, hydraulic, magnetic, electromagnetic, acoustic or/and mixed vibrations and contribute to the effective evacuation by the system 7 in regulated mode.

In the chamber 5, the cold-absorbing physical medium 6 interacts with the cooling medium 3, to which a vibratory action is applied, assuring the conditions of its cooling and its continuous functioning in stationary mode.

The regulated stream of the cold-absorbing physical medium 6 circulates, for example, in the stationary circuit. During its movement, the stream of physical medium 6 can be subjected to at least one vibratory action 10 for example by a radiation with microwaves, which creates an additional favourable condition of decontamination, disinfection and sterilisation of physical medium 6.

The aforesaid actions 11 and 13 establish the necessary and sufficient conditions for a pulverising of the physical medium 2 with fine dispersal, in the form of vapor and/or of aerosol and they prepare it for the process of fast cooling and/or freezing in the system 1.

Particles with fine dispersal of the cooling medium 3 cooled and/or frozen, for example, pure water coming into the chamber 1 in which they melt under the effect of a radiation 12, for example a microwaves radiation or another thermal or electromagnetic radiation, and are evacuated or/and circulate by the system 7 in regulated mode.

The present invention appeals to a process of simultaneous action on a physical medium 2 (FIG. 1), and/or on a cold-absorbing medium 6 by at least two vibratory actions, such as described first in the French patent N 96 02 080 of the same prosecutors.

However, unlike the invention described in the aforesaid application for a patent, the implementation of at least two vibratory actions on the treated media is used not for their mixture, but for their cold vaporisation and their cooling.

Within the framework of the present invention, the process according to the French patent N 96 02 080 is applied to conditioning, air conditioning, cooling and decontamination, disinfection, sterilisation of physical media in the following way.

According to the process described in the French patent N 96 02 080, in definite conditions, in an medium treated simultaneously by at least two vibratory actions, a vibratory treatment is performed, which breaks particles and molecules of the physical medium 2 (FIG. 1) into components, for example, molecules of the gas which form aerosol and/or vapour of the cooling medium 3 (FIG. 1).

The micronised molecules of the cooling medium 3 form a large surface, consume the energy of the heat brought by medium 6 and change their aggregation states. This interaction allows the heat exchange between media 3 and 6.

So, the process of vibratory treatment and of circulation of the various media by a series of actions on them, allows implementing their use with the evacuation devices of 7 and 8 (FIG. 1).

The invention claimed is:

1. A vibration method for conditioning, air conditioning, cooling and decontamination, disinfection, sterilisation, comprising the steps of:
    forming a refrigerant stream (3) of gas molecules of a cooled medium by simultaneously
    i) regulating a first vibratory action (13) to act on a regulated input stream (2) before entering a refrigerating heat exchanger (1), the input stream being a medium (2) comprised of particles and molecules of a refrigerant; and
    ii) regulating a second vibratory action (11) to act on the medium (2) before entering into the refrigerating heat exchanger (1),
    the first and second vibratory actions being regulated under conditions for micronisation and pulverising of the medium (2) into an aerosol when entering into the refrigerating heat exchanger (1),
    the first and second vibratory actions being regulated to create conditions of cooling the input stream and the medium (2) within the refrigerating heat exchanger to form the refrigerant stream (3),
    the first and second vibratory actions being different vibratory actions;
    in a chamber (5) of the refrigerating heat exchanger (1), interacting the refrigerant stream (3) with a cold-absorbing medium (6);
    within the chamber (5), applying a third vibratory action (10) to the cold-absorbing medium (6) sufficient to decontaminate the cold-absorbing medium;
    applying a fourth action (15) to the refrigerating stream (3) to circulate the refrigerating stream (3) with a first regulating device (7) within a closed circuit;
    applying a fifth action (14) to the cold-absorbing medium (6) to circulate the cold-absorbing medium (6) with a second regulating device (8) within another closed circuit; and
    regulating a regulator (9a) of a power supply source (9), to individually vary frequencies and energy amplitudes of each of the first vibratory action, the second vibratory action, the third vibratory action, and the fourth action and the fifth action, wherein,
    the frequency of the second vibratory action (11) differs from the frequency of the first vibratory action (13) by at least a factor of 10.

2. The method of claim 1, further comprising the step of regulating a further vibratory action (12) to act on the refrigerant stream (3) within said heat exchanger.

3. The method of claim 2, wherein,
    the first vibratory action (13) is a ultrasound action produced from one of a siren, a whistle, and a piezo-electric vibrator.

4. The method of claim 3, wherein,
    the second vibratory action (11) is a ultrasound action produced from one of a siren, a whistle, and a piezo-electric vibrator.

5. The method of claim 4, wherein,
    the further vibratory action (12) is a ultrasound action produced from one of a siren, a whistle, and a piezo-electric vibrator.

6. The method of claim 4, wherein,
    the further vibratory action (12) is produced from a magnetostriction device creating a magnetic or electromagnetic field.

7. The method of claim 3, wherein,
    the second vibratory action (11) is produced from a magnetostriction device creating a magnetic or electromagnetic field.

8. The method of claim 2, wherein,
    the first vibratory action (13) is produced from a magnetostriction device creating a magnetic or electromagnetic field.

9. The method of claim 2, wherein,
    the first vibratory action (13) is a ultrasound action produced from one of a siren, a whistle, and a piezo-electric vibrator in combination with a magnetic or electromagnetic field produced by a magnetostriction device.

10. The method of claim 9, wherein,
    the second vibratory action (11) is one of a ultrasound action produced from one of a siren, a whistle, and a piezo-electric vibrator and a magnetic or electromagnetic field produced by a magnetostriction device.

11. The method of claim 10, wherein,
    the further vibratory action (12) is one of a ultrasound action produced from one of a siren, a whistle, and a piezo-electric vibrator and a magnetic or electromagnetic field produced by a magnetostriction device.

12. The method of claim 1, wherein,
the regulated input stream (2) comprises a mixture of organic and inorganic substances, and
cold-absorbing medium (6) comprises another mixture of organic and inorganic substances.

13. The method of claim 1, wherein,
the third vibratory action (10) is produced by a magnetic device that creates a magnetic field.

14. The method of claim 1, wherein,
the third vibratory action (10) is produced by a device that creates a microwave field.

15. The method of claim 1, wherein,
when the first and second vibratory actions are regulated under conditions for micronisation, said pulverising of the medium (2) into an aerosol provides droplets lower than a micron in size when entering into the chamber of the refrigerating heat exchanger (1).

* * * * *